(12) United States Patent
Wang et al.

(10) Patent No.: US 8,461,384 B2
(45) Date of Patent: Jun. 11, 2013

(54) PREPARATION OF AMIDES FROM AN ACID AND AMINE FOR INTERMEDIATES IN THE SYNTHESIS OF MORPHINANS

(75) Inventors: Peter X. Wang, Chesterfield, MO (US); Frank W. Moser, Arnold, MO (US); Christopher W. Grote, Webster Groves, MO (US); Gary L. Cantrell, Troy, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 521 days.

(21) Appl. No.: 12/481,993

(22) Filed: Jun. 10, 2009

(65) Prior Publication Data
US 2009/0247760 A1    Oct. 1, 2009

Related U.S. Application Data

(62) Division of application No. 12/518,434, filed as application No. PCT/US2007/025263 on Dec. 10, 2007.

(60) Provisional application No. 60/874,131, filed on Dec. 11, 2006.

(51) Int. Cl.
*C07C 231/02* (2006.01)
*C07C 233/05* (2006.01)

(52) U.S. Cl.
USPC ............ 564/139; 564/182; 560/129; 558/248

(58) Field of Classification Search
USPC ................... 564/139, 182; 560/129; 558/248
See application file for complete search history.

(56) References Cited

U.S. PATENT DOCUMENTS

| 4,521,601 A | 6/1985 | Rice |
| 4,991,391 A | 2/1991 | Kosinski |
| 6,887,999 B1 | 5/2005 | Likhotvorik |

FOREIGN PATENT DOCUMENTS

| CN | 1115318 | 1/1996 |
| CN | 1115318 A | 1/1996 |
| DE | 922 827 | 1/1955 |
| WO | 01/55117 | 8/2001 |

OTHER PUBLICATIONS

Weller et al, J. Org. Chem., 1984, 2061-2063.*
Partial European Search Report dated Feb. 5, 2010.
Kitamura et al., "General Asymmetric Synthesis of Isoquinoline Alkaloids. Enantioselective Hydrogenation of enamides Catalyzed by BINAP-Ruthenium(II) Complexes", J. Org. Chem., 1994, 59, pp. 297-310, XP 002050844.
Bermejo et al., "Syntheses and Antitumor Targeting G1 Phase of the Cell Cycle of . . . ", Journal of Medicinal Chemistry, 2002, 45, pp. 5058-5068, XP 002302936.
Findelstein, "The Synthesis of dl-Claurine", J. Am. Chem. Soc., 73(2), 1951, pp. 550-553, XP 002565009.

Kametani et al., "Syntheses of heterocyclic compounds. CLXXV. Coclaurine and related compounds. 2. Syntheses of 7-benzyloxy-1,2,3,4-tetrahydro-1-(p-hydroxybenzyl)-6-methoxy-2-methylisoquinoline", Yakugaku Zasshi—Journal of the Pharmaceutical Society of Japan, Japan Science and Technology Information Aggregator, Electronic, JP, 87(7), 1967, pp. 757-760, XP 009127995.
Tolkachev et al., "Synthetic studies in the curare alkaloids area, XVI. Synthesis of 1-(3-bromo-4-methoxybenzyl)-67-dimethoxy-8-bromo-N-methyl-1,2,3,4-tetrahydroisoquinoline", Zhurnal Obshechei Khimii, Izdatel'Stvo Nauka, Sanky-Peterburgskoe Otdelenie, Russian Federation, 36(10), 1966, pp. 1767-1772, XP009127991.
Huang et al., "Synthesis of (+–)-Glaucine and (+–)-Neospirodienone via an One-Pot Bischler-Napieralski Reaction and Oxidative Coupling by a Hypervalent Iodine Reagent", Helvetica chimica Acta 2004 CH, vol. 887, No. 1, 2004, pp. 167-174, XP002476119.
Venkov et al., "Synthesis of isoquinolines from 2-phenylethylamines, amides, nitriles and carboxylic acids in polyphosphoric acid", Tetrahedron 19960909 GB, vol. 52, No. 37, Sep. 9, 1996, pp. 12299-12308, XP 002476120.
Beyerman et al., "Synthesis of racemic and optically active codeine and morphine via the N-formylnordihydrothebainones", Journal of the Royal Netherlands Chemical Society, 97, 5, May 1978, pp. 127-130.
Beyerman et al., "Synthesis of racemic and of ( + )- and ( – )-1 methyldihydrothebainone. (Chemistry of opium alkaloids, Part IV)", Recl. Trav. Chim. Pays-Bas, 1976, 75, p. 184-188.
Farber et al., "A Synthesis of Armepavine and Related Bases. Resolution of (±)-Armepavine", Anales. Asoc. Quim. Argentina, 58, 1970, pp. 133-138.
Farber et al., "Resolution of (±)-armepavine", Chemistry and Industry, Jan. 13, 1968, pp. 57-58.
Kametani et al., "131. Coclaurine 7-Benzyloxy-1,2,3,4-tetrahydro-1-(p-hydroxyphenyl)-6-methoxy-2-methylisoquinoline 7-Benzyloxy-1,2,3,4-tetrahydro-1-(p-hydroxybenzyl)-6-methoxy-2-methylisoquinoline", Coclaurine, vol. 87, No. 7, 1967, pp. 757-760.
Kashdan et al., "Synthesis of 1,2,3,4-Tetrahydroisoquinolines", J. Org. Chem., 1982, 47, pp. 2638-2643.
Kitamura et al., "General Asymmetric Synthesis of Isoquinoline Alkaloids. Enantioselective Hydrogenation of Enamides Catalyzed by BINAP-Ruthenium(II) Complexes", J. Org. Chem., 1994, 59, pp. 297-310.
Meuzelaar et al., "Chemistry of Opium Alkaloids, 45 Improvements in the Total Synthesis of Morphine", Eur. J. Org. Chem., 1999, pp. 2315-2321.
Nagata et al., "Synthetic Studies on Isoquinoline Alkaloids. I. An Efficient Synthesis of 9,10-Substituted Protoberberine Alkaloids", Chem. Pharm. Bull., 194, 23(11), pp. 2867-2877, 1975.
Saunders et al., "Assessment of relative nutritive value of proteins using streptoccus zymogenes", Chemistry and Industry, Jan. 13, 1968, pp. 56-58.

(Continued)

*Primary Examiner* — Shailendra Kumar

(57) ABSTRACT

The present invention is directed to processes for the synthesis of morphinans. In particular, a process for coupling a carboxylic acid compound with an amine compound to form an amide product that can then be isolated or the crude amide product can be cyclized to form a 3,4-dihydroisoquinoline. In one embodiment, the carboxylic acid contains a phenol moiety protected with a labile protecting group. The protected phenol reduces reaction times, simplifies work-up of the product, and reduces the amount of cyclizing agent, $POCl_3$ that is necessary to form the 3,4-dihydroisoquinoline.

14 Claims, No Drawings

OTHER PUBLICATIONS

Sheth et al., "Synthesis of N-(3',4'-Dimethoxy-5'-bromophenethyl)-2-(4"-hydrioxyphenyl)-acetamide & Allied Products", Indian Journal of Chemistry, vol. 15B, Jul. 1977, pp. 595-598.

Small et al., "The Addition of Organomagnesium Halides to Pseudocodeine Types. IV. Nuclear-Substituted Morphine Derivatives", Contribution from the Cobb Chemical Laboratory, University of Virginia, Received Jun. 6, 1938, pp. 204-232.

Uematsu et al., "Asymmetric Transfer Hydrogenation of Imines", J. Am. Chem. Soc., 1996, 118, pp. 4916-4917.

H.C. van der Plas et al., "On the reaction of 2-, 3- and 4-bromo(chloro)-1,8-naphthyridine with potassium amide in liquid ammonia", Laboratory of Organic Chemistry, Agricultural University, Wagenagen, The Netherlands.

Lespagnol et al., "Préparation d'amides de l'homovératrylamine et d'acides iodophénylacétiques substitués", Chim. Therap., 1965, 1, pp. 14-16.

Lespagnol et al., "Preparation of Amides From the Homoveratrylamine and Iodophenylacetic Substituted Acids", Chim. Therap., 1965, 1, pp. 14-16, Fast-Trans English Translation.

Tolkachev et al., "Synthetic Investigation in [Kurarealkaloidov] Area ", Organicheskoi Khimii, 1966, 36(10), pp. 1767-1772.

Tolkachev et al., "Synthetic Investigation in [Kurarealkaloidov] Area", English Translation of C18', 1965.

Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Greene et al., "Protection for Phenols", Protective Groups in Organic Synthesis, 3$^{rd}$, Ed., c1999, pp. 249-257and 266-269.

Plieninger Hans "Synthese des Desoxydauricins des N,N$^1$Dimethyl-desoxy-dauricins und einiger anderer curarewirksamer Verbindungen", Archiv der Pharmazie, 1953, 285-291.

Grewe et al, Die Synthese der Homoisovanillinsaure und ihre Uberfuhrung in 6-Methoxy-lsochinolin-Derivate, Chem. Ber. 1963, 1520-1528 (no. translation available).

Plieninger Hans "Synthese des Desoxydauricins des N,N'Dimethyl-desoxy-dauricins und einiger anderer curarewirksamer Verbindungen", Archive der Pharmazie, 1953, 285-291 (Partial english translation).

Farber, et al., Database Beilstein—Compound with Beilstein Registry No. 2789425 (Beilstein Institute for Organic Chemistry, 1970.

Fijjitani, et al., "Alkaloids of menispermaceous plants. CCXXIV. Syntheses of dauricine Type Bases. (1). Synthesis of 2-Hydroxy-5, 4'bis(2-methyl-6,7-dimethoxy-1,2,3,4-tetra-hydroisoquinolin-l-ylmethyl)-diphenyl Ether.", Yakugaku Zasshi—Journal of the Pharmaceutical Society of Japan, 1966, vol. 86(8), pp. 654-659.

Grewe, R., et al., "Die Synthese der Homoisovanillinsaure und ihre Uberfuhrung in 6-Methosy-isochinolin-Derivate," Chem. Ber., 1963, pp. 1520-1528.

Kratzl, et al., "Die synthese von 1-Benzylisochinolinen mit Guajacyl-Gruppierung," Monatshefte Fur Chemie, 1952, vol. 83, pp. 1409-1417.

Lespagnol, A., et al., "Etude de dihydro-isoquinoleines iodees," Chimie Therapeutique, 1968, vol. 3(3), pp. 173-175.

Nagata, W., et al., "Synthetic studies on isoquinoline alkaloids. I. An efficient synthesis of 9.10 substituted protoberberine alkaloids," 1975, pp. 2867-2877.

Sam, J., et al., "Modified synthesis of dl-N-norarmepavine and dl-armepavine," Journal of Pharmaceutical Sciences, 1967, vol. 56(7), pp. 906-908.

Sheldon, R.A., et al, "Chemistry of Opium Alkaloids, 45 . . . Improvements in Total Synthesis of Morphine," Eur. J. Org. Chem., 1999, pp. 2315-2321.

Tomita et al., "Studies on the alkaloids of menispermaceous plants. CCXL. Synthesis of cycleanine. (1). Cupric oxide catalysed ullmann condensation of dl-8-bromoarmepavine." 1967, vol. 15(12), pp. 1996-1999.

Weller, et al., "Preparation of Oxygenated Phenylacetic Acids," J. Org. Chem., 49, 1984, pp. 2061-2063.

Fryman, B. et al, A Synthesis of Laudanine and (+—) —Pseudo-Codamine: Resolution into the Optical Isomers; Tetrahedron; 1968, vol. 4, pp. 342-350.

Yamanaka et al., Shinpen Heterokankagobutsu Kisohen, 2005; pp. 236-377.

Whaley et al, The Preparation of 3,4-Dihydroisoquinolines and Related Compounds byt he Bischler-Napieralski Reaction; John Wiley & Sons, Inc.; 1960, p. 74-77, 98-9(Translator's note: p. 74-77, 98-9 is meant to be p. 74-74 and p. 98-99).

* cited by examiner

PREPARATION OF AMIDES FROM AN ACID AND AMINE FOR INTERMEDIATES IN THE SYNTHESIS OF MORPHINANS

RELATED APPLICATIONS

This application is a divisional of U.S. patent application Ser. No. 12/518,434 filed on Jun. 10, 2009 and entitled "PREPARATION OF 3,4-DIHYDROISOQUINOLINES FROM AN ACID AND AN AMINE", which claims priority to PCT application of PCT/US2007/025263, filed Dec. 10, 2007 and entitled "PREPARATION OF 3,4-DIHYDROISOQUINOLINES FROM AN ACID AND AN AMINE", which claims the benefit of U.S. Provisional Application No. 60/874,131 filed Dec. 11, 2006.

FIELD OF THE INVENTION

The present invention generally relates to processes for the synthesis of intermediates used to prepare morphinans. More specifically, the invention is directed to the synthesis of dihydroisoquinolines and their analogs.

BACKGROUND OF THE INVENTION

Dihydroisoquinolines are important synthetic intermediates to many morphinan compounds including burprenorphine, codeine, etorphine, hydrocodone, hydromorphone, morphine, nalbuphine, nalmefene, naloxone, naltrexone, oxycodone, and oxymorphone. Generally, these compounds are analgesics, which are used extensively for pain relief in the field of medicine due to their action as opiate receptor agonists. However, nalmefene, naloxone and naltrexone are opiate receptor antagonists; and are used for reversal of narcotic/respiratory depression due to opiate receptor agonists.

Rice (U.S. Pat. No. 4,521,601) discloses the reaction of 3-methoxy phenethylamine with 2-hydroxy-3-methoxyphenylacetic acid at 200° C. under argon. Generally, for a viable large scale production of the resulting amide compound, 200° C. is too high. For example, most large scale reaction vessels cannot routinely reach or sustain temperatures above 140° C.; thus, in order for large scale production of the morphinans, a special reactor or reactor heating unit is needed.

The Bischler-Napieralski cyclization generally converts an appropriately substituted amide to a 3,4-dihydroisoquinoline. Typically, when a free phenol group is present in the acid, and thus, also present in the amide, the cyclization requires more $POCl_3$, longer reaction times, and higher reaction temperatures, because the $POCl_3$ is known to react directly with the hydroxyl group of the phenol to produce phosphoryl halides. Reaction side products of poly-phosphates and incomplete hydrolysis of the phosphate groups usually result in decreased yields and difficult purification of the desired 3,4-dihydroisoquinoline products. Various protecting groups, particularly ether protecting groups, have been used to reduce the above problems in this cyclization step. However, use of these derivatives requires an additional synthetic step using harsh reagents and conditions to produce the free phenol. Thus, a need still exists for a synthetic method that requires reduced amounts of phosphorus oxychloride, lowered reaction times, reduced temperatures, simplified work-up and isolation, and does not require additional harsh synthetic steps to remove a phenol protecting group.

SUMMARY OF THE INVENTION

Among the various aspects of the present invention is a process for the preparation of a 3,4-dihydroisoquinoline corresponding to Formula 600 comprising treating an acid corresponding to Formula 300 with an amine corresponding to Formula 400. The 3,4-dihydroisoquinoline is produced without isolation or purification of reaction intermediates. The chemical structures for Formulae 300, 400, and 600 are

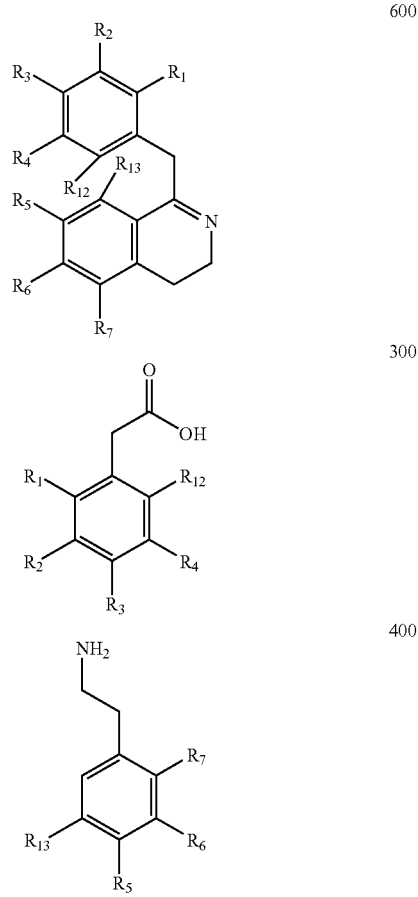

wherein $R_1$ and $R_7$ are independently hydrogen, hydrocarbyl, substituted hydrocarbyl, or $-OR_{111}$; $R_2$ is hydrogen, hydrocarbyl, substituted hydrocarbyl, halo, or $-OR_{211}$; $R_3$ is hydrogen, hydrocarbyl, substituted hydrocarbyl, or $-OR_{311}$; $R_4$ is hydrogen, hydrocarbyl, substituted hydrocarbyl, halo, or $-OR_{411}$; $R_5$ and $R_6$ are independently hydrogen, hydrocarbyl, substituted hydrocarbyl, or $-OR_{511}$; $R_{12}$ is hydrogen, hydrocarbyl, substituted hydrocarbyl, halo, or $-OR_{121}$; $R_{13}$ is hydrogen, hydrocarbyl, substituted hydrocarbyl, halo, or $-OR_{511}$; $R_{111}$ is hydrogen, hydrocarbyl, or substituted hydrocarbyl; $R_{211}$ is hydrogen, hydrocarbyl, $-C(O)R_{212}$, $-C(O)NHR_{213}$, or $-SO_2R_{214}$; $R_{212}$, $R_{213}$, and $R_{214}$ are independently hydrocarbyl or substituted hydrocarbyl; $R_{311}$ is hydrogen, hydrocarbyl, $-C(O)R_{312}$, $-C(O)NHR_{313}$, or $-SO_2R_{314}$; $R_{312}$, $R_{313}$, and $R_{314}$ are independently hydrocarbyl or substituted hydrocarbyl; $R_{411}$ is hydrogen, hydrocarbyl, $-C(O)R_{412}$, $-C(O)NHR_{413}$, or $-SO_2R_{414}$; $R_{412}$, $R_{413}$, and $R_{414}$ are independently hydrocarbyl or substituted hydrocarbyl; $R_{511}$ is hydrogen, hydrocarbyl, or substituted hydrocarbyl; and $R_{121}$ is hydrogen, hydrocarbyl, or substituted hydrocarbyl.

Another aspect of the invention is a process for the preparation of an amide corresponding to Formula 501 comprising treating an acid corresponding to Formula 301 with an amine corresponding to Formula 400. The chemical structures for Formulae 301, 400, and 501 are

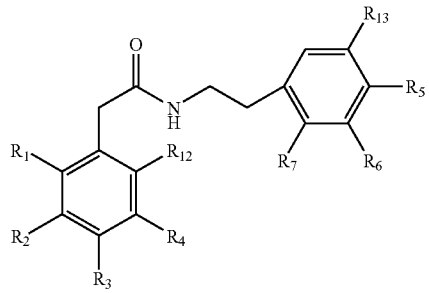

301

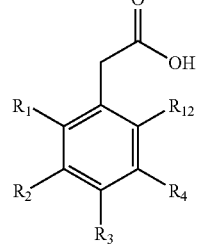

400

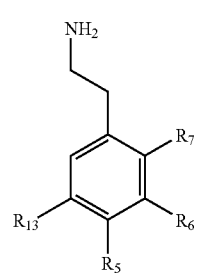

wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{313}$, $R_{411}$, $R_{413}$, $R_{414}$, $R_{511}$, and $R_{121}$ are defined above in connection with Formulae 300, 400, and 600; $R_{412}$ is alkyl or aryl, provided, $R_{412}$ is other than methyl or phenyl; $R_{312}$ is alkyl or aryl, provided, $R_{312}$ is other than methyl or phenyl; $R_{314}$ is alkyl or aryl, provided, $R_{314}$ is other than methyl; and wherein at least one of $R_2$, $R_3$, or $R_4$ is —OC(O)$R_{212}$, —OC(O)NH$R_{213}$, —OSO$_2$$R_{214}$, —OC(O)$R_{312}$, —OC(O)NH$R_{313}$, —OSO$_2$$R_{314}$, —OC(O)$R_{412}$, —OC(O)NH$R_{413}$, or —OSO$_2$$R_{414}$.

A further aspect of the invention is a process for the preparation of a 3,4-dihydroisoquinoline corresponding to Formula 601 comprising treating an amide corresponding to Formula 501 with up to about 1 equivalent of POCl$_3$. The chemical structures corresponding to Formulae 501 and 601 are

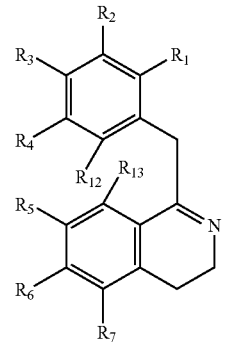

601

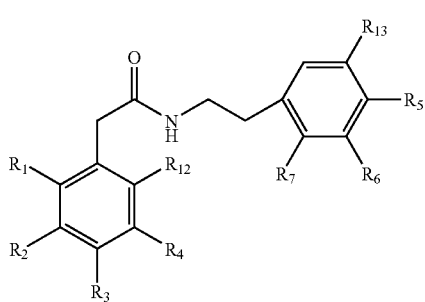

501 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{312}$, $R_{313}$, $R_{411}$, $R_{412}$, $R_{413}$, $R_{414}$, $R_{511}$, and $R_{121}$ are defined above in connection with Formulae 300, 400, and 600; and wherein at least one of $R_2$, $R_3$, or $R_4$ is —OC(O)$R_{212}$, —OC(O)NH$R_{213}$, —OSO$_2$$R_{214}$, —OC(O)$R_{312}$, —OC(O)NH$R_{313}$, —OSO$_2$$R_{314}$, —OC(O)$R_{412}$, —OC(O)NH$R_{413}$, or —OSO$_2$$R_{414}$.

Yet another aspect of the invention is a compound corresponding to Formula 502

502 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{313}$, $R_{411}$, $R_{413}$, $R_{414}$, $R_{511}$, and $R_{121}$ are defined above in connection with Formulae 300, 400, and 600; $R_{412}$ is alkyl or aryl, provided, $R_{412}$ is other than methyl or phenyl; $R_{312}$ is alkyl or aryl, provided, $R_{312}$ is other than methyl or phenyl; $R_{314}$ is alkyl or aryl, provided, $R_{314}$ is other than methyl: and wherein at least one of $R_2$, $R_3$, or $R_4$ is —OC(O)$R_{212}$, —OC(O)NH$R_{213}$, —OSO$_2$$R_{214}$, —OC(O)$R_{312}$, —OC(O)NH$R_{313}$, —OSO$_2$$R_{314}$, —OC(O)$R_{412}$, —OC(O)NH$R_{413}$, or —OSO$_2$$R_{414}$.

A further aspect of the invention is a compound corresponding to Formula 602

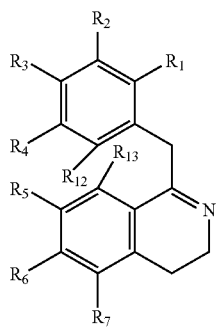

602 wherein $R_1$, $R_2$, $R_3$, $R_4$, $R_5$, $R_6$, $R_7$, $R_{12}$, $R_{111}$, $R_{211}$, $R_{212}$, $R_{213}$, $R_{214}$, $R_{311}$, $R_{313}$, $R_{411}$, $R_{413}$, $R_{414}$, $R_{511}$, and $R_{121}$ are defined above in connection with Formulae 300, 400, and 600; $R_{13}$ is hydrogen, hydrocarbyl, substituted hydrocarbyl, halo, or —$OR_{131}$; $R_{412}$ is alkyl or aryl, provided, $R_{412}$ is other than methyl or phenyl; $R_{312}$ is alkyl or aryl, provided, $R_{312}$ is other than methyl or phenyl; $R_{314}$ is alkyl or aryl, provided, $R_{314}$ is other than methyl; $R_{131}$ is hydrogen, hydrocarbyl, or substituted hydrocarbyl; and wherein at least one of $R_2$, $R_3$, or $R_4$ is —$OC(O)R_{212}$, —$OC(O)NHR_{213}$, —$OSO_2R_{214}$, —$OC(O)R_{312}$, —$OC(O)NHR_{313}$, —$OSO_2R_{314}$, —$OC(O)R_{412}$, —$OC(O)NHR_{413}$, or —$OSO_2R_{414}$.

Other objects and features will be in part apparent and in part pointed out hereinafter.

DETAILED DESCRIPTION OF THE INVENTION

The present invention is directed to an improved synthetic method for preparing 3,4-dihydroisoquinolines from a phenyl acetic acid derivative and an amine substituted benzene derivative. Among the various aspects of the present invention is the preparation of various 3,4-dihydroisoquinolines (Formulae 600, 601, and 602) from the reaction of particular phenyl acetic acid derivatives (Formulae 300 and 301) with phenethylamine derivatives (Formula 400). The reaction product of a phenyl acetic acid derivative and a phenethylamine derivative is an amide compound (Formulae 500, 501, and 502). In the synthetic method of the invention, the amide formed can be isolated or the crude product can be further reacted to form a 3,4-dihydroisoquinoline. Various phenyl acetic acid derivatives (Formula 301), amides (Formulae 501 and 502), and 3,4-dihydroisoquinolines (Formulae 601 and 602) of the invention are substituted with protecting groups to form ester, amide, or sulfonate ester moieties in order to facilitate the synthetic reactions and the isolation of intermediates.

Generally, the synthetic scheme for the processes of the invention as described above are depicted in Reaction Scheme 1 below.

Reaction Scheme 1

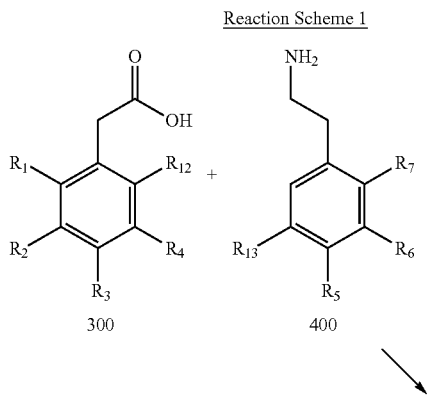

300   400

Each of these compounds and synthetic steps are described in more detail below.

3,4-Dihydroisoquinolines

As described above for Reaction Scheme 1, an aspect of the present invention is a process to prepare 3,4-dihydroisoquinolines corresponding to Formula 600

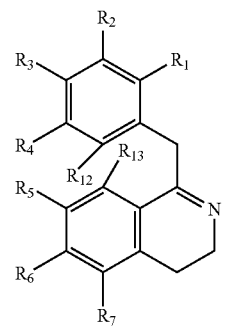

600 wherein
$R_1$ and $R_7$ are independently hydrogen, hydrocarbyl, substituted hydrocarbyl, or —$OR_{111}$;
$R_2$ is hydrogen, hydrocarbyl, substituted hydrocarbyl, halo, or —$OR_{211}$;
$R_3$ is hydrogen, hydrocarbyl, substituted hydrocarbyl, or —$OR_{311}$;
$R_4$ is hydrogen, hydrocarbyl, substituted hydrocarbyl, halo, or —$OR_{411}$;
$R_5$ and $R_6$ are independently hydrogen, hydrocarbyl, substituted hydrocarbyl, or —$OR_{511}$;
$R_{12}$ is hydrogen, hydrocarbyl, substituted hydrocarbyl, halo, or —$OR_{121}$;
$R_{13}$ is hydrogen, hydrocarbyl, substituted hydrocarbyl, halo, or —$OR_{511}$;
$R_{111}$ is hydrogen, hydrocarbyl, or substituted hydrocarbyl;
$R_{211}$ is hydrogen, hydrocarbyl, —$C(O)R_{212}$, —$C(O)NHR_{213}$, or —$SO_2R_{214}$;
$R_{212}$, $R_{213}$, and $R_{214}$ are independently hydrocarbyl or substituted hydrocarbyl;
$R_{311}$ is hydrogen, hydrocarbyl, —$C(O)R_{312}$, —$C(O)NHR_{313}$, or —$SO_2R_{314}$;
$R_{312}$, $R_{313}$, and $R_{314}$ are independently hydrocarbyl or substituted hydrocarbyl;
$R_{411}$ is hydrogen, hydrocarbyl, —$C(O)R_{412}$, —$C(O)NHR_{413}$, or —$SO_2R_{414}$;
$R_{412}$, $R_{413}$, and $R_{414}$ are independently hydrocarbyl or substituted hydrocarbyl;

$R_{511}$ is hydrogen, hydrocarbyl, or substituted hydrocarbyl; and $R_{121}$ is hydrogen, hydrocarbyl, or substituted hydrocarbyl.

In various embodiments, the 3,4-dihydroisoquinoline structure corresponds to Formula 601 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{312}$, $R_{313}$, $R_{314}$, $R_{411}$, $R_{412}$, $R_{413}$, $R_{414}$, $R_{511}$, and $R_{121}$ are defined as above for Formula 600; and wherein at least one of $R_2$, $R_3$, or $R_4$ is —OC(O)$R_{212}$, —OC(O)NH$R_{213}$, —OSO$_2R_{214}$, —OC(O)$R_{312}$, —OC(O)NH$R_{313}$, —OSO$_2R_{314}$, —OC(O)$R_{412}$, —OC(O)NH$R_{413}$, or —OSO$_2R_{414}$.

In some of the various embodiments, the 3,4-dihydroisoquinoline structure corresponds to Formula 602 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{313}$, $R_{411}$, $R_{413}$, $R_{414}$, $R_{511}$, and $R_{121}$ are defined as above for Formula 600; $R_{412}$ is alkyl or aryl, provided, $R_{412}$ is other than methyl or phenyl; $R_{312}$ is alkyl or aryl, provided, $R_{312}$ is other than methyl or phenyl; $R_{314}$ is alkyl or aryl, provided, $R_{314}$ is other than methyl; and wherein at least one of $R_2$, $R_3$, or $R_4$ is —OC(O)$R_{212}$, —OC(O)NH$R_{213}$, —OSO$_2R_{214}$, —OC(O)$R_{312}$, —OC(O)NH$R_{313}$, —OSO$_2R_{314}$, —OC(O)$R_{412}$, —OC(O)NH$R_{413}$, or —OSO$_2R_{414}$.

Although $R_2$ is hydrogen, hydrocarbyl, substituted hydrocarbyl, halo, or —OR$_{211}$, in some of the various embodiments, $R_2$ is hydrogen or —OR$_{211}$. In some of these embodiments, $R_{211}$ is hydrogen, alkyl, aryl, —C(O)$R_{212}$, —C(O)NH$R_{213}$, or —SO$_2R_{214}$. Preferably, $R_{211}$ is hydrogen, alkyl, or —C(O)$R_{212}$ wherein $R_{212}$ is alkyl or aryl. More preferably, $R_{211}$ is —C(O)$R_{212}$ wherein $R_{212}$ is methyl, ethyl, propyl, butyl, pentyl, hexyl, or phenyl. In some of the various embodiments, $R_{211}$ is —C(O)$R_{212}$ wherein $R_{212}$ is ethyl, propyl, butyl, pentyl, or hexyl.

Similarly, although $R_3$ is hydrogen, hydrocarbyl, substituted hydrocarbyl, or —OR$_{311}$, in some embodiments, $R_3$ is hydrogen or —OR$_{311}$. In some of these embodiments, $R_{311}$ is hydrogen, alkyl, aryl, —C(O)$R_{312}$, —C(O)NH$R_{313}$, or —SO$_2R_{314}$. Preferably, $R_{311}$ is hydrogen, alkyl, or —C(O)$R_{312}$ wherein $R_{312}$ is alkyl or aryl. More preferably, $R_{311}$ is —C(O)$R_{312}$ wherein $R_{312}$ is methyl, ethyl, propyl, butyl, pentyl, hexyl, or phenyl. In some of the various embodiments, $R_{311}$ is —C(O)$R_{312}$ wherein $R_{312}$ is ethyl, propyl, butyl, pentyl, or hexyl.

As noted above, $R_4$ is hydrogen, hydrocarbyl, substituted hydrocarbyl, halo, or —OR$_{411}$. In some embodiments, $R_4$ is hydrogen or —OR$_{411}$. In some of these embodiments, $R_{411}$ is hydrogen, alkyl, aryl, —C(O)$R_{412}$, —C(O)NH$R_{413}$, or —SO$_2R_{414}$. Preferably, $R_{411}$ is hydrogen, alkyl, or —C(O)$R_{412}$ wherein $R_{412}$ is alkyl or aryl. In some of the various embodiments, $R_{411}$ is —C(O)$R_{412}$ wherein $R_{412}$ is methyl, ethyl, propyl, butyl, pentyl, hexyl, or phenyl. More preferably, $R_{411}$ is —C(O)$R_{412}$ wherein $R_{412}$ is ethyl, propyl, butyl, pentyl, or hexyl.

Further, $R_6$ is hydrogen, hydrocarbyl, substituted hydrocarbyl, or —OR$_{511}$. In some embodiments, $R_6$ is hydrogen or —OR$_{511}$. In some of these embodiments, $R_{511}$ is hydrogen, alkyl, or aryl. Preferably, $R_{511}$ is hydrogen, methyl, ethyl, propyl, butyl, pentyl, hexyl, or phenyl; more preferably, methyl.

As noted above, $R_{12}$ is hydrogen, hydrocarbyl, substituted hydrocarbyl, halo, or —OR$_{121}$. In some embodiments, $R_{12}$ is hydrogen, alkyl, alkenyl, aryl, aralkyl, or halo. Preferably, $R_{12}$ is hydrogen, alkyl, allyl, benzyl, or halo.

In many of the various embodiments, $R_1$, $R_5$, $R_7$, and $R_{13}$ are hydrogen.

In combination, among the preferred embodiments are 3,4-dihydroisoquinolines corresponding to Formulae 600, 601, and 602 wherein $R_2$ is hydrogen or —OR$_{211}$ wherein $R_{211}$ is hydrogen, alkyl, or —C(O)$R_{212}$ wherein $R_{212}$ is alkyl or aryl. In some embodiments, $R_{212}$ is ethyl, propyl, butyl, pentyl, or hexyl. In these embodiments, $R_3$ is hydrogen or —OR$_{311}$. In various preferred embodiments, $R_{311}$ is hydrogen, alkyl, aryl, or —C(O)$R_{312}$, preferably, $R_{311}$ is hydrogen, alkyl, or —C(O)$R_{312}$ wherein $R_{312}$ is alkyl or aryl. In some of these embodiments, $R_{312}$ is ethyl, propyl, butyl, pentyl, or hexyl. Further, $R_4$ is hydrogen or —OR$_{411}$. In various embodiments, $R_{411}$ is hydrogen, alkyl, aryl, or —C(O)$R_{412}$, preferably, $R_{411}$ is hydrogen, alkyl, or —C(O)$R_{412}$ wherein $R_{412}$ is alkyl or aryl. In some embodiments, $R_{412}$ is methyl, ethyl, propyl, butyl, pentyl, hexyl, or phenyl. Alternatively, $R_{412}$ is ethyl, propyl, butyl, pentyl, or hexyl. Further yet, $R_6$ is hydrogen or —OR$_{511}$. In some of these embodiments, $R_{511}$ is hydrogen, methyl, ethyl, propyl, butyl, pentyl, hexyl, or phenyl; preferably, methyl. Additionally, $R_{12}$ is hydrogen, alkyl, allyl, benzyl, or halo. In many of these embodiments, $R_1$, $R_5$, $R_7$, and $R_{13}$ are hydrogen.

Amides

As described in Reaction Scheme 1, an amide corresponding to Formula 500 has the structure

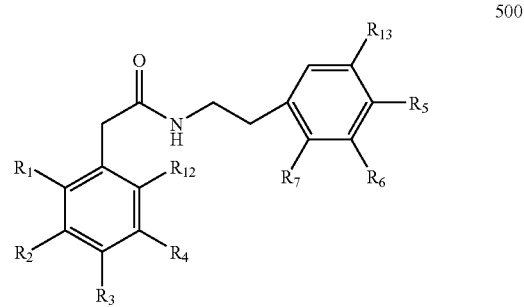

wherein $R_1$, $R_2$, $R_3$, $R_4$, $R_5$, $R_6$, $R_7$, $R_{12}$, and $R_{13}$ are defined as above in connection with Formula 600.

In some of the various embodiments of the invention, the amide corresponds to the structure of Formula 501 wherein $R_1$, $R_2$, $R_3$, $R_4$, $R_5$, $R_6$, $R_7$, $R_{12}$, and $R_{13}$ are defined as above in connection with Formula 600; and wherein at least one of $R_2$, $R_3$, or $R_4$ is —OC(O)$R_{212}$, —OC(O)NH$R_{213}$, —OSO$_2R_{214}$, —OC(O)$R_{312}$, —OC(O)NH$R_{313}$, —OSO$_2R_{314}$, —OC(O)$R_{412}$, —OC(O)NH$R_{413}$, or —OSO$_2R_{414}$.

In some of the various embodiments, the amide structure corresponds to Formula 502 wherein $R_1$, $R_2$, $R_3$, $R_4$, $R_5$, $R_6$, $R_7$, $R_{12}$, $R_{13}$, $R_{111}$, $R_{211}$, $R_{212}$, $R_{213}$, $R_{214}$, $R_{311}$, $R_{313}$, $R_{411}$, $R_{413}$, $R_{414}$, $R_{511}$, and $R_{121}$ are defined as above for Formula 600; $R_{412}$ is alkyl or aryl, provided, $R_{412}$ is other than methyl or phenyl; $R_{312}$ is alkyl or aryl, provided, $R_{312}$ is other than methyl or phenyl; $R_{314}$ is alkyl or aryl, provided, $R_{314}$ is other than methyl; and wherein at least one of $R_2$, $R_3$, or $R_4$ is —OC(O)$R_{212}$, —OC(O)NH$R_{213}$, —OSO$_2R_{214}$, —OC(O)$R_{312}$, —OC(O)NH$R_{313}$, —OSO$_2R_{314}$, —OC(O)$R_{412}$, —OC(O)NH$R_{413}$, or —OSO$_2R_{414}$.

Preferred substituent groups and preferred combinations of substituent groups for $R_1$, $R_2$, $R_3$, $R_4$, $R_5$, $R_6$, $R_7$, $R_{12}$, and $R_{13}$ are detailed above in connection with Formulae 600, 601, and 602.

In many of the various embodiments, a compound of Formula 500 having a free phenol group can be acylated or sulfonated to form a compound having a protected phenol group. For example, considering compounds of Formulae 510 to 512 below, Compound 510 can be acylated or sulfonated to form Compounds 511 and 512. The acylation of Compound 510 can occur using various acylating agents in the presence of an amine base. For example, acyl chlorides, anhydrides, pivaloyl chloride, or pivalic anhydride can be used to acylate Compound 510 to form Compound 511. For Compound 511, $R_{2a}$ is alkyl or aryl. In various preferred embodiments for Compound 511, $R_{2a}$ is alkyl or aryl, provided it is other than methyl and phenyl. Further, for the sulfonation of a compound of Formula 510, a variety of sulfonating agents can be used. For example, methanesulfonyl chloride can be used in the presence of an amine base to produce Compound 512. The solvent for the acylation or sulfonylation reactions can be selected from the group consisting of tetrahydrofuran, ethyl acetate, propyl acetate, toluene, xylene, acetonitrile and combinations thereof.

Compound 510

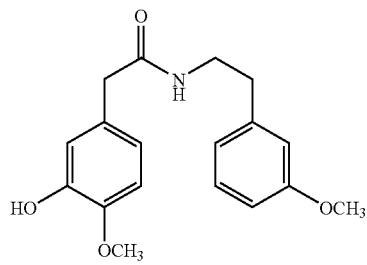

Compound 511

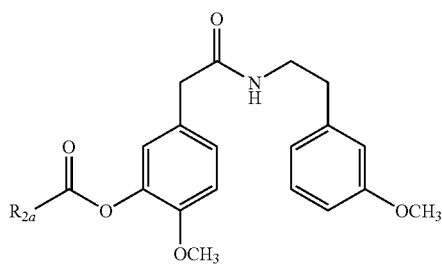

Compound 512

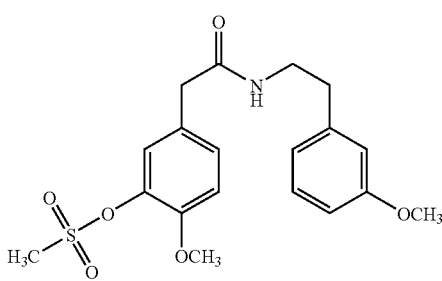

Carboxylic Acids

As described above in Reaction Scheme 1, carboxylic acids corresponding to Formula 300 have the structure

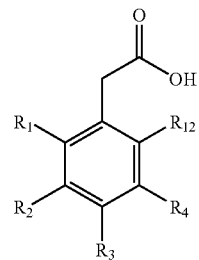

300 wherein $R_1$, $R_2$, $R_3$, $R_4$, and $R_{12}$ are defined as above in connection with Formula 600.

In some of the various embodiments of the invention, the carboxylic acid corresponds to the structure of Formula 301 wherein $R_1$, $R_2$, $R_3$, $R_4$, and $R_{12}$ are defined as above in connection with Formula 600; and wherein at least one of $R_2$, $R_3$, or $R_4$ is —OC(O)$R_{212}$, —OC(O)NHR$_{213}$, —OSO$_2$R$_{214}$, —OC(O)R$_{312}$, —OC(O)NHR$_{313}$, —OSO$_2$R$_{314}$, —OC(O)R$_{412}$, —OC(O)NHR$_{413}$, or —OSO$_2$R$_{414}$.

Preferred substituent groups and preferred combinations of substituent groups for $R_1$, $R_2$, $R_3$, $R_4$, and $R_{12}$ are detailed above in connection with Formulae 600, 601, and 602.

Compounds of Formula 300 and 301 are commercially available, and various esters, carbamates, and sulfonate esters of Formula 301 can be prepared by reacting the free phenol compound with the appropriate esterifying agent or amidation agent. For example, the following phenols (compounds of Formulae 310, 311, 312, and 313) correspond to the structures found below wherein $R_{12}$ is alkyl, allyl, or benzyl, and $R_{120}$ is halo. These phenols can be converted to the acetate form by reaction with acetyl chloride or acetic anhydride with or without the addition of a base. If a base is used, typical bases are selected from sodium acetate, potassium carbonate, sodium carbonate, sodium bicarbonate, potassium bicarbonate, triethylamine, diisopropylethylamine, dimethylaniline, N-methylmorpholine, pyridine, substituted pyridines (e.g., 4-dimethylamino pyridine) and combinations thereof.

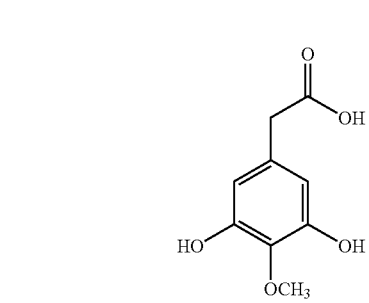

310

311

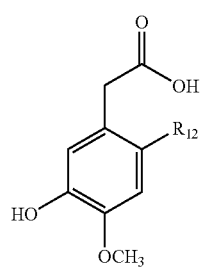

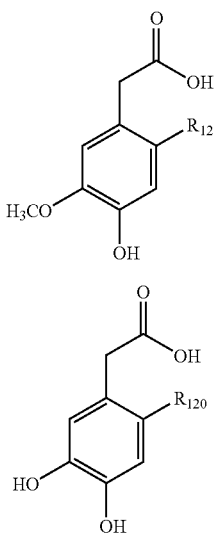

Amines

In connection with Reaction Scheme 1, amines corresponding to Formula 400 are used in various processes of the present invention

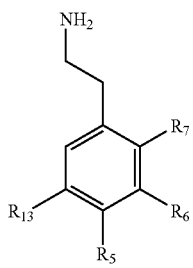

wherein $R_5$, $R_6$, $R_7$, and $R_{13}$ are defined as above in connection with Formula 600.

Preferred substituent groups and preferred combinations of substituent groups for $R_5$, $R_6$, $R_7$, and $R_{13}$ are detailed above in connection with Formulae 600, 601, and 602.

Compounds of Formula 400 are available commercially. For example, various methoxyphenethylamines and dimethoxyphenethylamines are available from Aldrich.

Reaction of a Carboxylic Acid and an Amine to Produce a 3,4-dihydroisoquinoline

For the process of the present invention, the structures of the products (e.g., 3,4-dihydroisoquinolines) and reactants (e.g., carboxylic acids and amines) are described above. This process of treating an amine with a carboxylic acid can occur in one vessel without isolation of intermediates. In certain embodiments, the coupling reaction of the carboxylic acid and amine is performed under anhydrous conditions. These anhydrous conditions can be obtained, for example, by removal of water by distillation or by addition of a water scavenging agent. Removal of water by distillation can occur at discrete time points during the reaction or it can be continuous. For example, use of a Dean-Stark trap provides for continuous removal of water. Also, water can be removed from the reaction mixture by contact with a water scavenger. The water scavenger may be added separately from the other components of the reaction mixture or, alternatively, it may be pre-mixed with one of the components and the mixture is then combined with the remaining components. In general, the water scavenger is preferably a composition that absorbs the water. Exemplary substances that absorb water include anhydrous inorganic salts that form hydrates (e.g., magnesium sulfate), molecular sieves and the like.

In some of the various embodiments, the solvent comprises an aprotic solvent. For example, particularly preferred solvents are xylene, toluene, acetonitrile, ethyl acetate, propyl acetate, tetrahydrofuran, and combinations thereof. Depending on the starting materials and solvent, the temperature and time of the coupling reaction can vary. For example, when a carboxylic acid containing an unprotected phenol moiety is coupled with an amine in refluxing xylene (135° C. to 145° C.) with continuous removal of water by Dean-Stark trap, the coupling reaction takes approximately 14 hours. In contrast, when a carboxylic acid containing a protected phenol moiety is coupled with an amine in acetonitrile, the reaction is complete upon reaction for 1 hour at 50° C. and an additional 1 hour at reflux (approximately 78° C.). In some of the various embodiments, the temperature of the reaction is from about 25° C. to about 100° C.; preferably, from about 40° C. to about 90° C.; more preferably, from about 50° C. to about 80° C.

Once the coupling reaction of the carboxylic acid and the amine is complete, the amide produced can be isolated (as described in more detail below) or the crude product can undergo a Bischler-Napieralski cyclization by treatment with $POCl_3$ to produce the desired 3,4-dihydroisoquinoline. Preferably, during the treatment with $POCl_3$, anhydrous conditions are used. In certain embodiments of the present invention, up to about 1 equivalent of $POCl_3$ is used to cyclize the amide to form the desired 3,4-dihydroisoquinoline. In some embodiments, when about 0.5 equivalent $POCl_3$ is used to cyclize the amide in refluxing toluene, the reaction time is approximately 48 hours. In various embodiments, the carboxylic acid containing a protected phenol moiety is combined with the $POCl_3$ and heated before it is contacted with a mixture containing the amine and an amine base. This reaction mixture is then heated to 50° C. for 1 hour and then to reflux in acetonitrile (approximately 78° C.) for another hour.

In many of the various embodiments, a carboxylic acid with a protected phenol moiety is used in the coupling reaction. The phenol moiety can be protected with a variety of labile protecting groups to form groups such as esters, carbamates, and sulfonate esters. For example, the carboxylic acid reactants used in these embodiments correspond to Formula 301 as described above. Use of these carboxylic acids having protected phenol moieties provides advantages over use of corresponding carboxylic acids that are not protected with such labile protecting groups. For example, the coupling reaction of the carboxylic acid and amine occurs at a lower temperature and takes less time. Specifically, the reaction of 2-acetoxy-3-methoxyphenyl acetic acid with 2-methoxyphenethylamine and $POCl_3$ to form the corresponding 3,4-dihydroisoquinoline takes 2 hours at 50-78° C. as compared to 14 hours at 140° C. for the same reactants with the substitution of 2-hydroxy-3-methoxyphenyl acetic acid for 2-acetoxy-3-methoxyphenyl acetic acid.

Also, the reaction work-up and isolation of products are improved when such phenol protected carboxylic acids are used as starting materials. The 3,4-dihydroisoquinolines obtained from the process using the protected phenol group are obtained in higher yield. Upon reaction work up, addition of aqueous base removes the phenol protecting group and forms the salt. This salt precipitates (or crystallizes) at room temperature, thus producing high quality crystals. A pH adjustment to approximately pH 5 or 6 converts the salt to the phenol.

Coupling Reaction of a Carboxylic Acid and an Amine to form an Amide

In various embodiments, the amide intermediate (Formula 500, 501, and 502) is isolated before reaction with $POCl_3$ to form the desired 3,4-dihydroisoquinoline. Preferably, the amide intermediate isolated corresponds to Formula 501 or 502. Amides corresponding to Formula 501 and 502 have a phenol moiety protected with a labile protecting group as described above. The reaction conditions and solvents used for the coupling reaction are described above. Generally, the amide can be isolated by washing with an aqueous acid solution (e.g., HCl) and an aqueous salt solution (e.g., NaCl) followed by removal of the reaction solvent.

Bischler-Napieralski Cyclization of an Amide to a 3,4-dihydroisoquinoline

When the amide corresponding to Formulae 500, 501, or 502 is isolated, this isolated amide can undergo a Bischler-Napieralski cyclization to form a 3,4-dihydroisoquinoline by treatment of the amide with $POCl_3$.

Generally, the reaction conditions for this cyclization and isolation and purification procedures for the 3,4-dihydroisoquinoline product include an azeotropic distillation of the amide, $POCl_3$ addition and reaction, distillation to remove toluene and excess $POCl_3$, and reaction work-up. In various embodiments, preferably, about 1.10 to about 5.0 equivalents of $POCl_3$ are used. When fewer equivalents of $POCl_3$ are used a higher temperature (e.g., about 90° C.) is needed. When more equivalents of $POCl_3$ are used a lower temperature (e.g., about 60° C.) is needed. Preferably, the reaction time is from about 2 to about 9 hours. The reaction progress is monitored by in process liquid chromatography. This reaction is described in more detail in Examples 3 and 4.

Uses of Intermediates

The above-described synthesis stages are important in the preparation of morphinans and analogs thereof. General reaction schemes for the preparation of morphinans are disclosed in U.S. Pat. No. 4,368,326 to Rice, the entire disclosure of which is incorporated by reference. The morphinans and analogs thereof (i.e., the morphinans contain an X group of N—($R_{17}$) or $N^+$-($R_{17a}R_{17b}$)) of interest in the practice of the present invention are opiate receptor agonists or antagonists and generally are compounds corresponding to Formula (24)

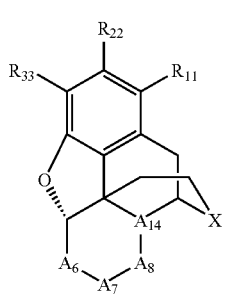

(24)

wherein -$A_6$-$A_7$-$A_8$-$A_{14}$- corresponds to Formulae (S), (T), (U), (V), (W), (X), (Y), or (Z):

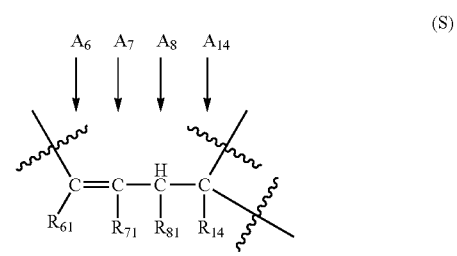

(S)

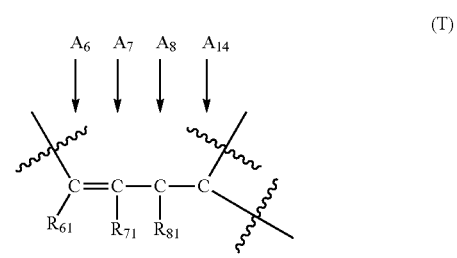

(T)

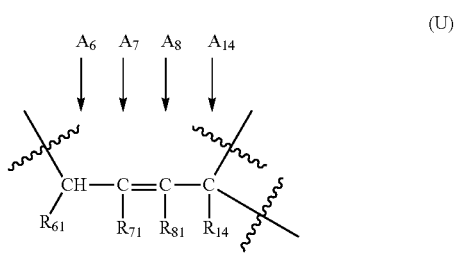

(U)

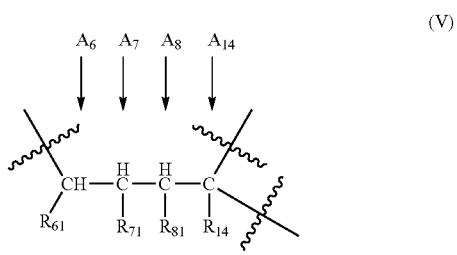

(V)

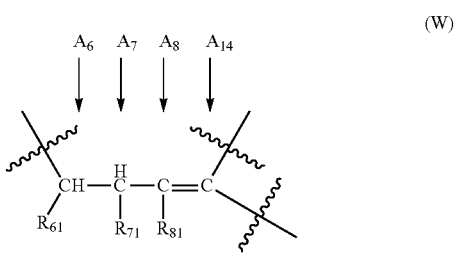

(W)

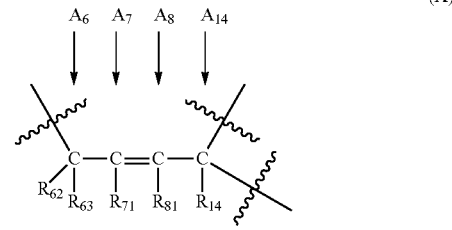

(X)

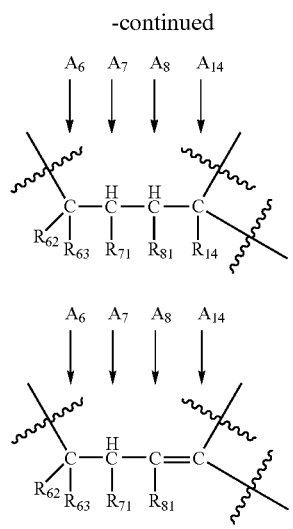

$R_{11}$ and $R_{22}$ are independently hydrogen, substituted and unsubstituted acyl, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxy, protected hydroxy, or nitro;

$R_{14}$ is hydrogen, acyloxy, hydroxy, or protected hydroxy;

$R_{17}$ is hydrogen, alkyl, alkoxy, alkylenecycloalkyl, allyl, alkenyl, acyl, formyl, formyl ester, formamide, or benzyl;

$R_{17a}$ and $R_{17b}$ are independently hydrogen, alkyl, cycloalkyl, cycloalkylalkyl, aryl, or benzyl;

$R_{18}$ and $R_{19}$ are independently hydrogen, substituted and unsubstituted acyl, alkenyl, alkoxy, alkoxyaryl, alkyl, alkylamino, arylthio, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, halo, haloalkoxy, haloalkyl, heteroaryl, heterocyclic, hydroxyalkyl, hydroxy, or nitro, or $R_{18}$ and $R_{19g}$ together form keto;

$R_{33}$ is alkoxy, acyloxy, hydroxy, or protected hydroxy;

$R_{61}$ is alkoxy, acyloxy, hydroxy, or protected hydroxy;

$R_{62}$ and $R_{63}$ are independently hydrogen, alkyl, alkenyl, alkynyl, allyl, alkoxy, alkylthio, acyloxy, or aryl, together form keto, or together with the carbon atom to which they are attached form a ketal, dithioketal, or monoketal;

$R_{71}$ and $R_{81}$ are independently hydrogen, hydrocarbyl, substituted hydrocarbyl, or halo; and X is oxygen, sulfur, —S(O)—, —S(O$_2$)—, —C(R$_{18}$)(R$_{19}$)—, —N(R$_{17}$)—, or —N(R$_{17a}$R$_{17b}$)—.

In a particular embodiment, the products and intermediates produced according to the present invention are useful in the preparation of a morphinan compound corresponding to Formula (24) wherein X is —N(R$_{17}$)— and R$_{17}$ is defined as above.

For purposes of clarity, the carbon atoms of Formulae (S), (T), (U), (V), (W), (X), (Y), and (Z) corresponding to $A_6$, $A_7$, $A_8$, and $A_{14}$ of Formula (24), respectively, have been identified (by indicating with an arrow which carbon atom corresponds to each). Further, squiggly lines have been included in Formulae (S), (T), (U), (V), (W), (X), (Y), and (Z) to indicate the points of attachment to the polycyclic ring of Formula (24).

Exemplary morphinans that may be produced according to a variety of methods include, for instance, nordihydrocodeinone (i.e., Formula (24) wherein $R_{11}$, $R_{17}$, and $R_{22}$ are hydrogen, $R_{33}$ is methoxy, X is —N(R$_{17}$)—, and -A$_6$-A$_7$-A$_8$-A$_{14}$- corresponds to Formula (Y) wherein $R_{14}$ is hydrogen, $R_{62}$ and $R_{63}$ together form keto, and $R_{71}$ and $R_{81}$ are hydrogen) (which corresponds to Formula (241) below); dihydrocodeinone (i.e., Formula (24) wherein $R_{11}$ and $R_{22}$ are hydrogen, $R_{17}$ is methyl, $R_{33}$ is methoxy, X is —N(R$_{17}$)—, and -A$_6$-A$_7$-A$_8$-A$_{14}$- corresponds to Formula (Y) wherein $R_{14}$ is hydrogen, $R_{62}$ and $R_{63}$ together form keto, and $R_{71}$ and $R_{81}$ are hydrogen) (which corresponds to Formula (242) below); noroxymorphone (i.e., Formula (24) wherein $R_{11}$, $R_{17}$, and $R_{22}$ are hydrogen, $R_{33}$ is hydroxy, X is —N(R$_{17}$)—, and -A$_6$-A$_7$-A$_8$-A$_{14}$- corresponds to Formula (Y) wherein $R_{14}$ is hydroxy, $R_{62}$ and $R_{63}$ together form keto, and $R_{71}$ and $R_{81}$ are hydrogen) (which corresponds to Formula (243) below); and salts, intermediates, and analogs thereof.

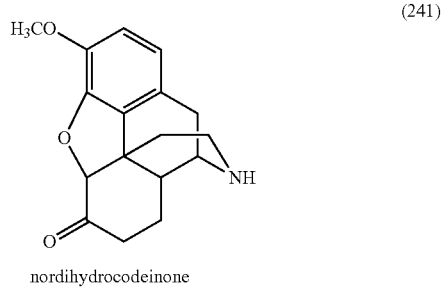

nordihydrocodeinone (241)

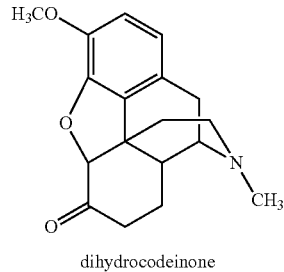

dihydrocodeinone (242)

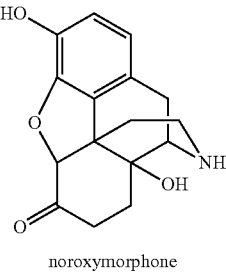

noroxymorphone (243)

DEFINITIONS

The term "acyl," as used herein alone or as part of another group, denotes the moiety formed by removal of the hydroxyl group from the group COOH of an organic carboxylic acid, e.g., RC(O)—, wherein R is R$_1$, R$_1$O—, R$_1$R$_2$N—, or R$_1$S—, R$_1$ is hydrocarbyl, heterosubstituted hydrocarbyl, or heterocyclo, and R$_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

Having described the invention in detail, it will be apparent that modifications and variations are possible without departing from the scope of the invention defined in the appended claims.

EXAMPLES

The following non-limiting examples are provided to further illustrate the present invention.

Example 1

Preparation of Compound 511 from Compound 510

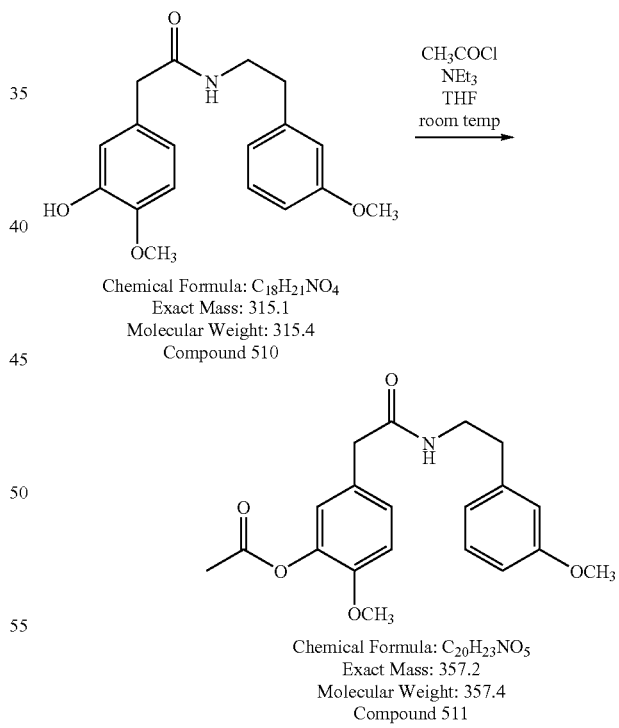

Into the reaction flask was placed Compound 510 (254.6 g, 0.81 moles, 1.0 eq) and anhydrous tetrahydrofuran (THF, inhibitor free, 1.0 L). After cooling the mixture to 0° C., triethylamine (89.86 g, 0.89 moles, 1.10 eq) was added dropwise. Then, acetyl chloride (66.54 g, 0.85 moles, 1.05 eq) was added dropwise while maintaining the temperature below 10° C. The reaction mixture was warmed to room temperature and stirred until the reaction was shown to be complete by HPLC monitoring. Generally, reaction time ranged from 1.0 to 4.0 hours. The reaction mixture was filtered and the filtrate was evaporated to a thick oil of the crude acetate. This thick oil was dissolved in ethyl acetate (500 mL) and washed with 1.0M HCl (3×100 mL) and saturated NaCl (1×100 mL). After drying over anhydrous MgSO$_4$, filtering, and evaporating the ethyl acetate, the crude Compound 511 was isolated as a thick oil. Yield=89%. In various experiments, the reaction yield for this reaction ranged from 85% to 98%.

Generally, 1.1 to 1.25 equivalents of NEt$_3$ (triethylamine) and 1.05 to 1.20 equivalents of acetyl chloride are preferably used. Because of the aqueous work-up and wash with 1.0M HCl, excess acetyl chloride and triethyl amine were removed during the work-up.

In various experiments, acetic anhydride or pivaloyl chloride was substituted for acetyl chloride.

Example 2

Preparation of Compound 512 from Compound 510

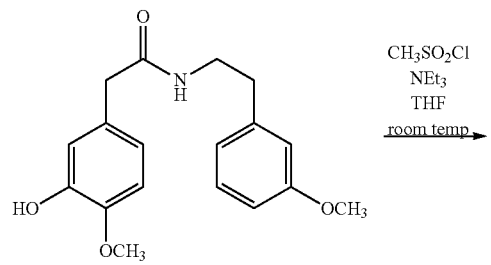

Chemical Formula: C$_{18}$H$_{21}$NO$_4$
Exact Mass: 315.1
Molecular Weight: 315.4
Compound 510

Chemical Formula: C$_{19}$H$_{23}$NO$_6$S
Exact Mass: 393.1
Molecular Weight: 393.5
Compound 512

Into the reaction flask was placed Compound 510 (40.60 g, 0.13 moles, 1.0 eq) and anhydrous tetrahydrofuran (THF, inhibitor free, 300 mL). After cooling the mixture to 0° C., triethylamine (16.28 g, 0.16 moles, 1.25 eq) was added dropwise. Then, methanesulfonyl chloride (17.69 g, 0.15 moles, 1.15 eq) was added dropwise while maintaining the temperature below 10° C. The reaction mixture was warmed to room temperature and stirred until the reaction was shown to be complete by HPLC; approximately 4 hours, but for convenience, 14 hours. The reaction mixture was filtered and the filtrate was evaporated to a thick oil of crude Compound 512. This thick oil was dissolved in ethyl acetate (100 mL) then washed with 1.0M HCl (3×100 mL) and saturated NaCl (1×100 mL). After drying over anhydrous MgSO$_4$, filtering, and evaporating the ethyl acetate, the crude Compound 512 was isolated as a thick oil. Yield=95%.

Generally, preferably, 1.1 to 1.25 equivalents of NEt$_3$ (triethylamine) and 1.05 to 1.20 equivalents of methanesulfonyl chloride are used. Because of the aqueous work-up and wash with 1.0M HCl, excess methane sulfonyl chloride and triethyl amine were removed during the work-up.

Example 3

Preparation of Compound 610 from Compound 511

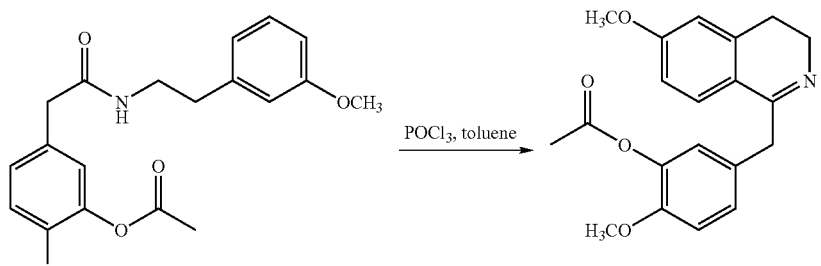

Chemical Formula: C$_{20}$H$_{23}$NO$_5$
Exact Mass: 357.2
Molecular Weight: 357.4
Compound 511

Chemical Formula: C$_{20}$H$_{21}$NO$_4$
Exact Mass: 339.1
Molecular Weight: 339.4

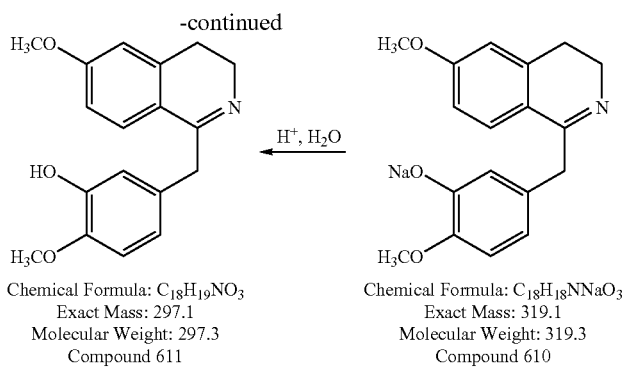

Chemical Formula: C$_{18}$H$_{19}$NO$_3$
Exact Mass: 297.1
Molecular Weight: 297.3
Compound 611

Chemical Formula: C$_{18}$H$_{18}$NNaO$_3$
Exact Mass: 319.1
Molecular Weight: 319.3
Compound 610

The crude Compound 511 (256.0 g, 0.72 moles, 1.0 eq) was dissolved in toluene (500 mL). A short path distillation apparatus was affixed to the reaction flask. Under reduced pressure, approximately 250 mL of reaction solvent was removed. After removing the vacuum and cooling the reaction flask to room temperature under inert atmosphere, phosphorus oxychloride (120.8 g, 0.79 moles, 1.1 eq) was added dropwise. The reaction was warmed to 70° C. and stirred for 2 hours. HPLC analysis showed complete reaction. The reaction was cooled to room temperature, the addition funnel was removed, and the short path distillation apparatus was affixed. Under reduced pressure, the reaction mixture was distilled to a thick oil. The reaction mixture was cooled to OC. To the reaction flask, 300 mL distilled water and 300 mL methanol were slowly added. After stirring the reaction mixture for 1 hour with fast stirring, 50% NaOH/H$_2$O solution (approximately 125 mL) was added until the pH was maintained at 14. This mixture was stirred for 12 hours at room temperature. An off-white precipitate formed. This solid was filtered and washed with 250 mL distilled water and 250 mL heptane. After drying at elevated temperature, 225.2 g (98% yield) of Compound 610 was obtained.

In various experiments, the reaction yield ranged from 90% to 98%. Due to the distillation after reaction, excess POCl$_3$ (BP: 106° C.) was removed by distillation. During the work-up, NaOH was added to raise the pH to about 14, thus resulting in Compound 610. Upon reducing the pH to 5 the phenol Compound 611 is formed.

Example 4

Preparation of Compound 610 from Compound 512

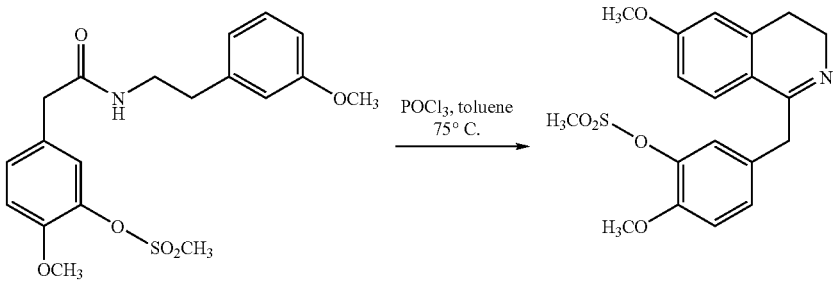

Chemical Formula: C$_{19}$H$_{23}$NO$_6$S
Exact Mass: 393.1
Molecular Weight: 393.5
Compound 512

Chemical Formula: C$_{19}$H$_{21}$NO$_5$S
Exact Mass: 375.1
Molecular Weight: 375.4

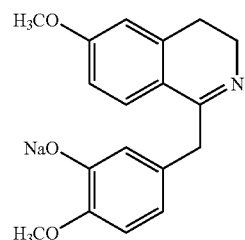

Chemical Formula: C$_{18}$H$_{18}$NNaO$_3$
Exact Mass: 319.1
Molecular Weight: 319.3
Compound 610

The crude Compound 512 (48.3 g, 0.12 moles, 1.0 eq) was dissolved in toluene (400 mL). A short path distillation apparatus was affixed to the reaction flask. Under reduced pressure, approximately 150 mL of reaction solvent was removed. After removing the vacuum and cooling the reaction mixture to room temperature under inert atmosphere, phosphorus oxychloride (28.23 g, 0.18 moles, 1.5 eq) was added dropwise. The reaction mixture was warmed to 50° C. and stirred for 2 hours, followed by warming to 75° C. and stirring for 4 hours. HPLC analysis showed complete reaction. The reaction mixture was cooled to 50° C., the addition funnel was removed, and the short path distillation apparatus was affixed. Under reduced pressure, the reaction mixture was distilled to a thick oil and cooled to 0° C. To the reaction flask, 100 mL distilled water and 100 mL methanol was slowly added. After stirring the reaction for 1 hour with fast stirring, 50% NaOH/$H_2O$ solution (approximately 25 mL) was added until the pH was maintained at 14. This mixture was stirred for 18 hours at room temperature. An off-white precipitate formed. This solid was filtered and washed with 50 mL distilled water and 50 mL heptane. After drying at elevated temperature, 32.2 g (82% yield) of Compound 610 was obtained.

Example 5

Preparation of Compound 510 from reaction of Compound 315 and Compound 410

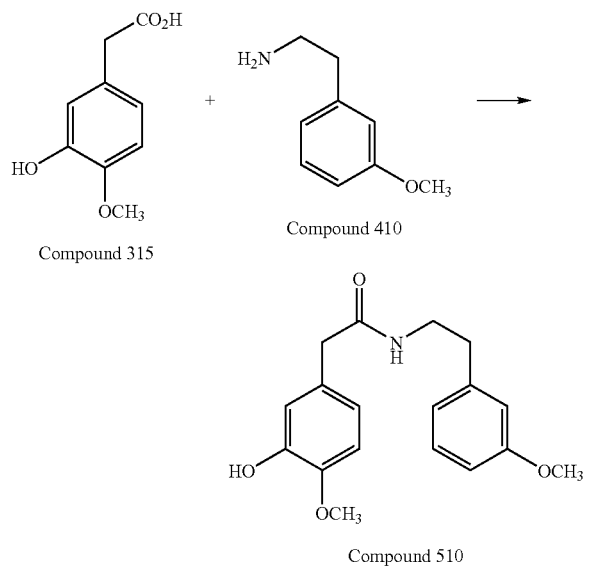

Compound 315 and xylene (3.5 mL/g of Compound 315) were added to a reactor equipped with a mechanical stirrer and a Dean-Stark apparatus. Then, a solution of Compound 410 (0.85 g/g of Compound 315) in xylene (1.5 mL/g of Compound 315) was added. The reaction suspension was heated at reflux for 14 hours with collection of water (~0.1 mL/g of Compound 315). Further distillation removed 80% of the xylene (4.0 mL/g of Compound 315). The remaining thick liquid was cooled to 70° C. and ethyl acetate (4.0 mL/g of Compound 315) followed by heptane (2.0 mL/g of Compound 315) was added at 70° C. with good stirring. The resulting solution was cooled to 15° C. for 2.5 hours with stirring to give crystals. The solid was separated by filtration, washed with ethyl acetate/heptane (1:1, 0.75 mL/g of Compound 315), washed with hexane (1.0 mL/g of Compound 315) and dried under flowing air for 1 hour. Further drying under vacuum (20 inches) at 45° C. for 20 hours gave the product (Compound 510) as off-white crystals. The yield ranged from 90% to 95%.

Example 6

Preparation of Compounds 611 and 612 from Compound 510

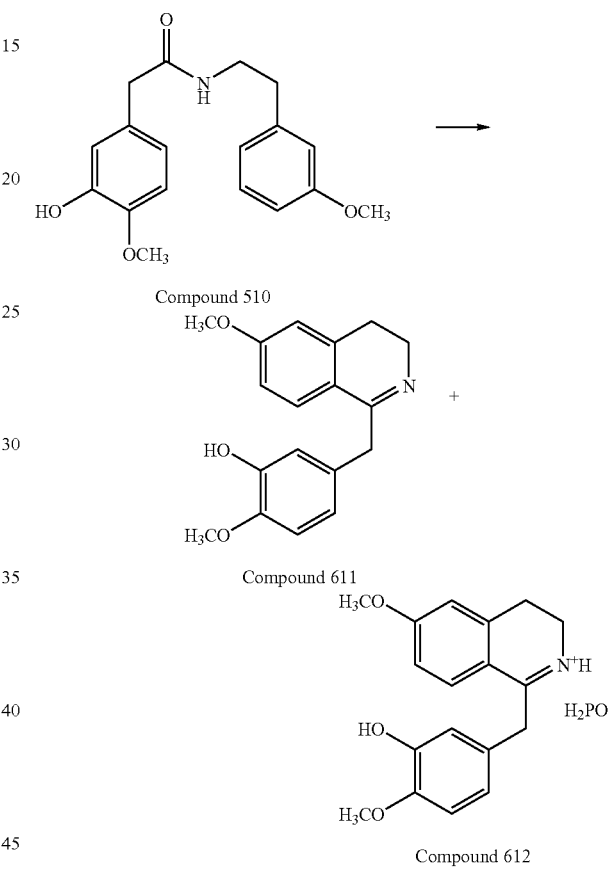

Compound 510 $POCl_3$ (0.89 mL/g of Compound 510) and acetonitrile (4.0 mL/g of Compound 510) were added to a reactor equipped with a mechanical stirrer and a condenser. The reaction suspension was stirred and heated to 50° C. for 2 hours and then further heated to reflux for 1 hour followed by cooling to 25° C. The resulting solution was slowly added to water (4.0 mL/g of Compound 510) with stirring. The temperature of this exothermic mixture was maintained below 70° C. during the addition and then the mixture was heated to 70° C. for 60 minutes after the addition was complete. The solution was treated with sodium hydroxide (50%, about 1.50 to 2.5 g/g of Compound 510) until the pH was between 4.2 and 4.8. Solvent (4.2 mL/g of Compound 510) was removed by distillation and water (3.2 mL/g of Compound 510) was added. The reaction mixture was heated to reflux for 6 hours and cooled to 75° C. with good stirring. Acetonitrile (1.0 mL/g of Compound 510) was added and the pH was adjusted to about 4.4 to 4.6. The reaction mixture was heated to reflux for 30 minutes and cooled to 10° C. with good stirring to form crystals. The solid was separated by filtration, washed with water (3×0.5 mL/g of Compound 510), and dried under vacuum (20 inches) at 60° C. for 20 hours to give the product as a yellow crystals (a mixture of 611 and 612).

Example 7

Preparation of Compound 611 from Compound 612

Water (2.33 mL/g of Compound 612), methanol (1.33 mL/g of Compound 612) and concentrated hydrochloric acid (37%, 0.33 mL/g of Compound 612) were added to a flask equipped with a mechanical stirrer. Compound 612 was added with stirring to form a solution. The pH of the solution was adjusted to between 0.0 to 0.8 with concentrated hydrochloric acid or concentrated ammonium hydroxide. Activated carbon (0.10 g/g of Compound 612) was added and the mixture was heated at 45° C. for 30 minutes and filtered through a bed of celite (0.10 g/of Compound 613). The solid residue was washed with a hot solution of 0.5N hydrochloric acid in water/methanol (prepared by mixing 1N HCl/H$_2$O with methanol in a volumetric ratio of 1:11 pH=0.00 to 0.80) three times (3×0.60 mL/g of Compound 612). The combined filtrate and washes were added, dropwise, to a well stirred solution of 28% ammonium hydroxide (2.00 mL/g of Compound 613) in water (2.00 mL/g of Compound 613) at 10° C. to form a suspension (pH about 10). The pH was adjusted to about 9.0 to 10.0 with concentrated hydrochloric acid or concentrated ammonium hydroxide. The reaction mixture was stirred for another 2 hours at 10° C. and filtered. The solid was washed with water (3×0.67 mL/g of Compound 613), dried under vacuum (20 inches) at 60° C. for 20 hours to give the product as an off-white solid. The yield ranged from 85% to 90% based on Compound 510.

Example 8

Preparation of Compound 611 from Compound 315 and Compound 410

A mixture of Compound 315 (24.4 g) and Compound 410 (20.2 g) was refluxed in p-xylene (75 mL) with the continuous removal of water using a Dean-Stark apparatus in an 165° C. oil bath for 16 hours. Most of the solvent was removed by distillation. The last trace of the solvent was distilled under reduced pressure (about 40 to 80 mmHg) in an oil bath maintained at 165° C. The mixture was then quickly cooled to 75° C. to give a thick liquid. Acetonitrile (200 mL) was added at that temperature to form a brownish solution followed by cooling to less than 50° C. Phosphorus oxychloride (40 mL) was added dropwise. The mixture was stirred at less than 50° C. for 2 hours and then was heated to reflux for 1 hour. The mixture was cooled to less than 50° C. and added to water (200 mL). The solution was treated with sodium hydroxide (50%) until the pH was 4.5 and then heated to reflux for 8 hours until hydrolyzed. Solvent was removed by distillation until the vapor temperature reached 95° C. Acetonitrile (20 mL) was added and the solution was cooled to 5 to 10° C. with vigorous stirring to form a solid. The crude product was obtained as off white crystals after filtration in yields of 50-75%.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A process for the preparation of an amide corresponding to Formula 502, the process comprising treating an acid corresponding to Formula 301 with an amine corresponding to Formula 400 under anhydrous conditions and at a temperature of from about 25° C. to about 100° C. to form the amide corresponding to Formula 502:

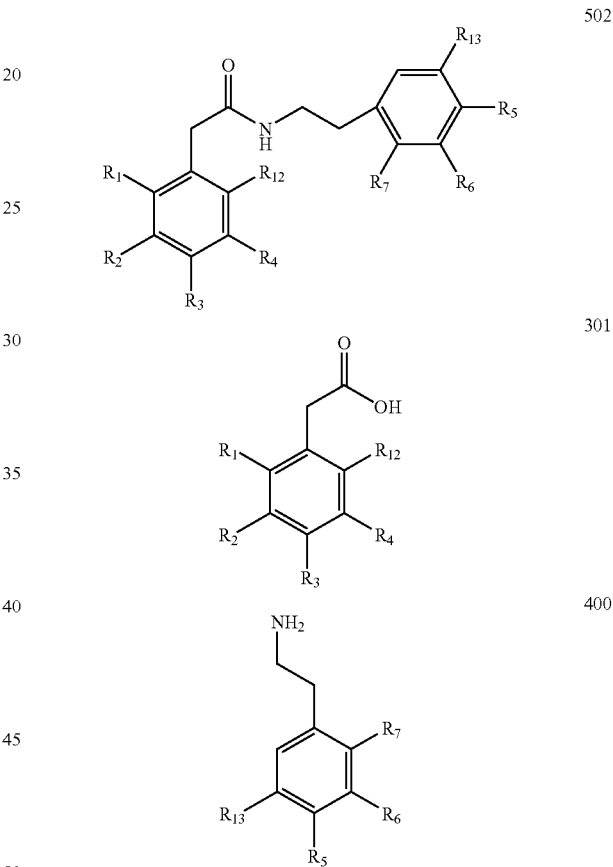

wherein
R$_1$ and R$_7$ are independently hydrogen, hydrocarbyl, substituted hydrocarbyl, or —OR$_{111}$;
R$_2$ is hydrogen, hydrocarbyl, substituted hydrocarbyl, halo, or —OR$_{211}$;
R$_3$ is hydrogen, hydrocarbyl, substituted hydrocarbyl, or —OR$_{311}$;
R$_4$ is hydrogen, hydrocarbyl, substituted hydrocarbyl, halo, or —OR$_{411}$;
R$_5$ and R$_6$ are independently hydrogen, hydrocarbyl, substituted hydrocarbyl, or —OR$_{511}$;
R$_{12}$ is hydrogen, hydrocarbyl, substituted hydrocarbyl, halo, or —OR$_{121}$;
R$_{13}$ is hydrogen, hydrocarbyl, substituted hydrocarbyl, halo, or —OR$_{511}$;
R$_{111}$ is hydrogen, hydrocarbyl, or substituted hydrocarbyl;

$R_{211}$ is hydrogen, hydrocarbyl, —C(O)$R_{212}$, —C(O)NH$R_{213}$, or SO$_2$$R_{214}$;

$R_{212}$, $R_{213}$, and $R_{214}$ are independently hydrocarbyl or substituted hydrocarbyl;

$R_{311}$ is hydrogen, hydrocarbyl, —C(O)$R_{312}$, —C(O)NH$R_{313}$, or —SO$_2$$R_{314}$;

$R_{312}$ is alkyl or aryl, provided, $R_{312}$ is other than methyl or phenyl;

$R_{313}$ is hydrocarbyl or substituted hydrocarbyl;

$R_{314}$ is alkyl or aryl, provided, $R_{314}$ is other than methyl;

$R_{411}$ is hydrogen, hydrocarbyl, —C(O)$R_{412}$, —C(O)NH$R_{413}$, or —SO$_2$$R_{414}$;

$R_{412}$ is alkyl or aryl, provided, $R_{412}$ is other than methyl or phenyl;

$R_{413}$ and $R_{414}$ are independently hydrocarbyl or substituted hydrocarbyl;

$R_{511}$ is hydrogen, hydrocarbyl, or substituted hydrocarbyl; and $R_{121}$ is hydrogen, hydrocarbyl, or substituted hydrocarbyl; wherein at least one of $R_2$, $R_3$, or $R_4$ is —OC(O)$R_{212}$, —OC(O)NH$R_{213}$, —OSO$_2$$R_{214}$, —OC(O)$R_{312}$, —OC(O)NH$R_{313}$, —OSO$_2$$R_{314}$, —OC(O)$R_{412}$, —OC(O)NH$R_{413}$, or —OSO$_2$$R_{414}$.

2. The process of claim 1, wherein:
$R_2$ is —O$R_{211}$;
$R_{211}$ is hydrogen, alkyl, —C(O)$R_{212}$, —C(O)NH$R_{213}$, or —SO$_2$$R_{214}$; and
$R_{212}$, $R_{213}$, and $R_{214}$ are independently hydrocarbyl or substituted hydrocarbyl.

3. The process of claim 1, wherein:
$R_3$ is —O$R_{311}$;
$R_{311}$ is hydrogen, alkyl, —C(O)$R_{312}$, —C(O)NH$R_{313}$, or —SO$_2$$R_{314}$;
$R_{312}$ is alkyl or aryl, provided, $R_{312}$ is other than methyl or phenyl;
$R_{313}$ is hydrocarbyl or substituted hydrocarbyl; and
$R_{314}$ is alkyl or aryl, provided, $R_{314}$ is other than methyl.

4. The process of claim 1, wherein:
$R_4$ is —O$R_{411}$;
$R_{411}$ is hydrogen, alkyl, —C(O)$R_{412}$, —C(O)NH$R_{413}$, or —SO$_2$$R_{414}$;
$R_{412}$ is alkyl or aryl, provided, $R_{412}$ is other than methyl or phenyl; and
$R_{413}$ and $R_{414}$ are independently alkyl or aryl.

5. The process of claim 1, wherein $R_{12}$ is alkyl, allyl, benzyl, or halo.

6. The process of claim 1, wherein $R_3$ is methoxy, $R_4$ is hydroxyl, —OC(O)CH$_2$CH$_3$, or —OSO$_2$CH$_3$, $R_6$ is methoxy, and $R_1$, $R_2$, $R_5$, $R_7$, $R_{12}$, and $R_{13}$ are hydrogen.

7. The process of claim 1, wherein:
$R_2$ is —O$R_{211}$;
$R_{211}$ is hydrogen, alkyl, —C(O)$R_{212}$, —C(O)NH$R_{213}$, or —SO$_2$$R_{214}$;
$R_{212}$, $R_{213}$, and $R_{214}$ are independently hydrocarbyl or substituted hydrocarbyl;
$R_3$ is —O$R_{311}$;
$R_{311}$ is hydrogen, alkyl, —C(O)$R_{312}$, —C(O)NH$R_{313}$, or —SO$_2$$R_{314}$;
$R_{312}$ is alkyl or aryl, provided, $R_{312}$ is other than methyl or phenyl;
$R_{313}$ is hydrocarbyl or substituted hydrocarbyl;
$R_{314}$ is alkyl or aryl, provided, $R_{314}$ is other than methyl;
$R_4$ is —O$R_{411}$,
$R_{411}$ is hydrogen, alkyl, —C(O)$R_{412}$, —C(O)NH$R_{413}$, or —SO$_2$$R_{414}$;
$R_{412}$ is alkyl or aryl, provided, $R_{412}$ is other than methyl or phenyl; and
$R_{413}$ and $R_{414}$ are independently alkyl or aryl.

8. The process of claim 7, wherein $R_{12}$ is alkyl, allyl, benzyl, or halo.

9. The process of claim 7, wherein $R_{212}$, $R_{213}$, $R_{214}$, $R_{313}$, $R_{413}$, and $R_{414}$ are methyl.

10. The process of claim 7, wherein $R_{12}$ is alkyl, allyl, benzyl, or halo; and $R_{212}$, $R_{213}$, $R_{214}$, $R_{313}$, $R_{413}$, and $R_{414}$ are methyl.

11. The process of claim 1, wherein anhydrous conditions are obtained by removal of water from the reaction mixture by distillation.

12. The process of claim 1, wherein anhydrous conditions are obtained by addition of a water scavenging agent to the reaction mixture.

13. The process of claim 1, wherein the temperature of the reaction mixture is from about 40° C. to about 90° C.

14. A compound corresponding to Formula 502:

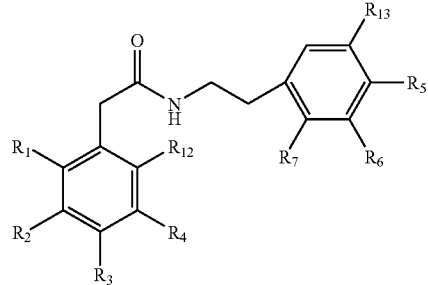

wherein
$R_1$ and $R_7$ are hydrogen,
$R_2$ is hydrogen;
$R_3$ is methoxy;
$R_4$ is —OC(O)CH$_3$ or —OSO$_2$CH$_3$;
$R_5$ is hydrogen;
$R_6$ is methoxy;
$R_{12}$ is hydrogen; and
$R_{13}$ is hydrogen.

* * * * *